United States Patent [19]

Parris et al.

[11] Patent Number: 4,684,755

[45] Date of Patent: Aug. 4, 1987

[54] CATALYZED PROCESS

[75] Inventors: David Parris; Steven P. Tonner, both of Melbourne, Australia

[73] Assignee: ICI Australia Limited, Victoria, Australia

[21] Appl. No.: 908,207

[22] Filed: Sep. 17, 1986

[30] Foreign Application Priority Data

Sep. 27, 1985 [AU] Australia ............................ PH2661

[51] Int. Cl.[4] ........................ C07C 5/02; C07C 5/327
[52] U.S. Cl. ................................... 585/257; 585/656
[58] Field of Search ............................... 585/257, 656

[56] References Cited

U.S. PATENT DOCUMENTS

| | | | |
|---|---|---|---|
| 3,267,170 | 8/1966 | Aldridge et al. | 585/257 |
| 3,267,171 | 8/1966 | Mattox | 585/257 |
| 3,321,545 | 5/1967 | Rigney et al. | 585/257 |
| 3,524,898 | 8/1970 | Beirne | 585/257 |
| 4,546,204 | 10/1985 | Parris et al. | |

Primary Examiner—Curtis R. Davis
Attorney, Agent, or Firm—Cushman, Darby & Cushman

[57] ABSTRACT

A transhydrogenation process for the conversion of alkanes to alkenes with high yields and extended catalyst life between regenerations comprises the pssing of an alkane combined with a suitable hydrogen acceptor over a catalyst bed, subject to the conditions that
  (a) the pressure is from 0-4 atmospheres (gauge);
  (b) the hydrogen acceptor is present to the extent of from 5-30% by volume;
  (c) the temperature of the catalyst is from 400°-600° C.; and
  (d) the temperature of the catalyst is raised during the process at a rate of from 1-15 deg. C/hr.

The catalyst is preferably a chromia on alumina type.

14 Claims, No Drawings

CATALYZED PROCESS

This invention relates to an improved transhydrogenation process.

Transhydrogenation is a process whereby a mixture of at least two hydrocarbons, at least one of which is an alkane and at least one of which is an alkene, is fed to a catalyst bed, and in the subsequent reaction, the alkane becomes an alkene and the alkene an alkane. This process can be used for the synthesis of alkenes, either as finished materials or for use as starting materials in further synthesis. Examples of existing processes can be found in, for example, Australian patent application No. AU-A-34694/84 and U.S. Pat. Nos. 3,321,545, 3,267,170 and 3,267,171. In the known art, a wide range of process conditions such as temperatures, pressures, and proportions of reactants has been specified.

It is essential, of course, that such processes be run as efficiently as possible. One important aspect of this requirement is that the catalyst should last as long as possible between regenerations. This aspect is, however, one which has been largely neglected by the art.

We have now found that it is possible, by careful regulation of process parameters, to have a transhydrogenation process which is appreciably more efficient in its utilisation of catalyst than are known processes. We therefore provide, according to the present invention, a process for the transhydrogenation of a blend of hydrocarbons comprising at least one alkene which acts as a hydrogen acceptor and at least one alkane, wherein the blend is contacted with a transhydrogenation catalyst, the process being subject to the following parameters;

(a) the pressure is from atmospheric pressure to four atmospheres (gauge);
(b) the hydrogen acceptor is present to the extent of from 5-30% by volume of the blend;
(c) the temperature of the catalyst is from 400° C.-600° C.; and
(d) during the process, the temperature of the catalyst is raised at a rate of from 1-15 deg C. per hour.

We have found that the implementation of these process conditions confers on the catalyst an unusually long working life before there is a need for regeneration.

The alkanes and alkenes for use in the process are of course selected such that the required final product or products will be given. The alkane which is to be converted to an alkene by the process according to this invention may be selected from a wide range of suitable materials. It may be, for example, a pure alkane, or a blend of such alkanes. The blend may be a hydrocarbon feedstock from a prior cracking operation, which comprises a blend of alkanes with quantities of other hydrocarbons.

The hydrogen acceptor may be selected from any alkenes known to the art to be suitable for this purpose. As a general rule, ethylene and propylene are the most suitable and these are our preferred hydrogen acceptors, but other alkenes may also be used. The hydrocarbons are fed to the catalyst, typically at a GHSV of from 0.1-1 hr.$^{-1}$. The GHSV (gaseous hourly space velocity) is a parameter well known to the art and is defined as $$\frac{\text{gaseous flow rate of hydrocarbon feed}}{\text{volume of catalyst}}$$

It is a requirement of our process that the concentration of hydrogen acceptor at the catalyst be kept to 5-30% by volume (preferably 10-25%) of the total hydrocarbon feed. This, of course, will limit the output from a single bed of catalyst, but an acceptably high overall output may be obtained by utilising several catalyst beds in series and splitting the feed of hydrogen acceptor between them such that no one catalyst bed is exposed to a concentration in excess of 30%.

The catalysts for use in this invention may be selected from any catalyst known to the art to catalyse transhydrogenation reactions. Our preferred catalysts are the oxides of chromium, vanadium and zinc. These may be used without catalyst supports, but we have obtained best results by using them in conjunction with alumina supports of surface area of from 80-300 m$^2$g$^{-1}$ (preferably 100-200 m$^2$g$^{-1}$). The concentration of metal oxide present in such a system should be between 1% and 20% (preferably between 2% and 12%) by weight of catalyst plus support. The catalyst may be used in any convenient form; it may, for example, be powdered, granular or moulded into spheres or pellets.

A particularly preferred catalyst for the purposes of our invention is the chromia on alumina type. Such catalysts are well known to and widely used by the art. We have found that in order to achieve the best results in our process, these catalysts should be subjected to particular reducing and regenerating regimes. Prior to use, the catalyst should be heated in a reducing atmosphere. This is carried out over a period of from 0.5-24 hours at a temperature of from 300° to 700° C. (preferably from 400° to 550° C.), and suitable reducing gases include hydrogen and carbon monoxide and mixtures thereof; these mixtures may be diluted with inert diluent gases.

When the catalyst is to be regenerated, it should preferably be done by heating in an oxygen-containing gas flow at a temperature of from 300° to 700° C., preferably from 300° to 500° C. The initial gas flow should preferably contain less than 10% more preferably less than 5% and most preferably less than 2% by volume of oxygen but this can thereafter be increased until air is used.

The pressure of the reactants should be from atmospheric to four atmospheres (gauge), preferably from atmospheric to two atmospheres (gauge). This is relatively low compared to what has been proposed in the past for use in transhydrogenation processes, but we have found it essential that these pressures be used. The catalyst should be used at a temperature of from 400° to 600° C., preferably from 440° to 520° C.

We have found it essential not only that the temperature of the catalyst be restricted within the abovementioned range, but also that this temperature be raised gradually during the process at a rate of from 1 to 15 deg. C. per hour (preferably from 5-10 deg. C. per hour). When the upper temperature limit is reached, the catalyst is subjected to regeneration. We believe this temperature rise to be an especially important feature of our invention as it permits the efficient utilisation of the catalyst.

We have found that, as a result of our process, the time during which a catalyst gives useful performance before regeneration is needed is greatly extended, with consequent cost savings.

The invention is further illustrated by the following examples.

EXAMPLES 1-8

(a) Preparation of catalyst

An alumina support (ex Harshaw Chemical Company) of particle size 500-700 μm and surface area 131 $m^2g^{-1}$ was impregnated with chromic acid such that the support particles had a loading of 7.6% by weight of chromium after drying at 110° C. for 16 hours. The support was then calcined at 500° C. for 9 hours.

(b) Preparation of catalyst bed

The catalyst prepared as hereinabove described was packed into a stainless steel tubular reactor and held in place with glass beads and glass wool. The reactor was then placed inside a tubular electric furnace equipped with means for regulating temperature and rate of temperature increase. Prior to reaction, the catalyst was reduced at 500° C. for 1.5 hr. in a flow of 5% (volume) hydrogen in nitrogen, the flow rate being 100 $cm^3$ $min.^{-1}$.

(c) Transhydrogenation

A blend of isobutane and ethylene was fed into the reactor at a GHSV of 0.25 $hr^{-1}$, proportions and conditions being as set down in the following table. The reaction products were analysed by gas chromatography using a flame ionisation detector.

When transhydrogenation had been carried out for a given set of parameters, the catalyst was regenerated at 400°-500° C. using an oxygen/nitrogen blend, wherein the quantity of oxygen was 3% by volume.

| Example No. | 1 | 2 | 3 | 4 | 5 | 6 | 7 | 8 |
|---|---|---|---|---|---|---|---|---|
| Pressure (atm. (gauge)) | 0.5 | 0.5 | 0.5 | 0.5 | 2.0 | 4.0 | 2.0 | 2.0 |
| Ethylene Concn. (Vol %) | 20 | 20 | 21 | 32 | 23 | 23 | 23 | 22 |
| Initial Temperature (°C.) | 450 | 450 | 450 | 450 | 450 | 450 | 450 | 450 |
| Rate of temperature increase (deg C/hr.) | 5 | 5 | 5 | 5 | 10 | 10 | 10 | 0 |
| Initial isobutane conversion (%) | 29 | 29 | 30 | 40 | 28 | 26 | 28 | 27 |
| Run time (min.) | 719 | 948 | 564 | 560 | 320 | 310 | 202 | 206 |
| Final temperature (°C.) | 510 | 530 | 497 | 497 | 504 | 501 | 484 | 450 |
| Isobutane conversion[1] (%) | 26 | 17 | 28 | 15 | 23 | 9 | 23 | 12 |
| Isobutene selectivity[2] (%) | 96 | 93 | 96 | 95 | 96 | 94 | 97 | 98 |

[1]isobutane conversion = $\frac{\text{moles isobutane converted}}{\text{moles isobutane fed}} \times 100$

[2]isobutene selectivity = $\frac{\text{moles isobutene formed}}{\text{moles isobutane converted}} \times 100$ The examples may be considered in pairs, 1 and 2, 3 and 4, 5 and 6, and 7 and 8; in each pair, the odd-numbered example lies within the preferred embodiment of the invention, and the even-numbered one lies outside this embodiment.

(a) Example 1 and 2. In this case, the final temperature of Example 2 is 530° C., that is, outside the preferred temperature range. This has a deleterious effect on the isobutane conversion.

(b) Example 3 and 4. Here, the ethylene concentration of Example 4 exceeds the 30% maximum. Again, the isobutane conversion is seen to suffer.

(c) Examples 5 and 6. This demonstrates the advisability of low pressures, Example 6 adhering to the upper limit of the preferred embodiment. The falling-off in isobutane conversion is quite notable.

(d) Examples 7 and 8. In this case, Example 8 has no gradual increase of catalyst temperature. There is a resultant drop in isobutane conversion.

This overall effect of this series of examples is to demonstrate conclusively the necessity of adhering to the parameters of the present invention, particularly the preferred parameters.

EXAMPLE 9

The transhydrogenation of propane.

The procedures of Example 1-8 were repeated using a blend of propane and ethylene, the ethylene being present to the extent of 23% by volume. The blend was passed over the catalyst of Examples 1-8 at a flow rate (GHSV) of 0.4 $hr.^{-1}$ at atmospheric pressure (0 atmospheres (gauge)) and at an initial temperature of 450° C. The temperature was raised at the rate of 10 deg. C./hr until 470° C. was reached, then at 5 deg. C./hr until 505° C. was reached, at which point the feed was stopped. The total feed time was 420 minutes and the results achieved were as follows:

propane conversion at initial temperature 18%
propene selectivity at initial temperature 94%
propane conversion (after 420 minutes) 18%
propene selectivity (after 420 minutes) 97%

We claim
1. A process for the transhydrogenation of a blend of hydrocarbons comprising at least one alkene which acts as a hydrogen acceptor, and at least one alkane, wherein the blend is contacted with a transhydrogenation catalyst under the following conditions:
 (a) the pressure of the blend at the catalyst is from atmospheric pressure to four atmospheres (gauge);
 (b) the hydrogen acceptor is present in the blend to the extent of from 5-30% of the volume thereof;
 (c) the temperature of the catalyst is from 400° C. to 600° C.; and
 (d) during the process, the temperature of the catalyst is raised at the rate of from 1 to 15 deg. C. per hour.

2. A process according to claim 1 wherein the pressure of the blend at the catalyst is from atmospheric pressure to two atmospheres (gauge).

3. A process according to claim 1 wherein the hydrogen acceptor is present in the blend to the extent of from 10-25% of the volume thereof.

4. A process according to claim 1, wherein the temperature of the catalyst is from 440° to 520° C.

5. A process according to of claim 1, wherein the rate of temperature increase of the catalyst is from 5 to 10 deg. C. per hour.

6. A process according to claim 1, wherein the catalyst is chosen from the oxides of chromium, vanadium and zinc.

7. A process according to claim 6, wherein the catalyst is used in conjunction with an alumina support of surface area of from 80-300 $m^2g^{-1}$.

8. A process according to claim 7, wherein the surface area of the aluminium support is from 100-200 $m^2g^{-1}$.

9. A process according to claim 7, wherein the concentration of metal oxide present is from 1% to 20% by weight of catalyst plus support.

10. A process according to claim 9, wherein the concentration is from 2% to 12% by weight of catalyst plus support.

11. A process according to claim 6, wherein the catalyst is regenerated by heating in a gas flow initially containing no more than 10% by volume of oxygen at a temperature of from 400° to 600° C.

12. A process according to claim 11, wherein the initial gas flow contains no more than 5% by volume of oxygen.

13. A process according to claim 11, wherein the initial gas flow contains no more than 2% by volume of oxygen.

14. A process according to claim 11, wherein the temperature range is from 200° to 500° C.

* * * * *